United States Patent [19]

Reid

[11] Patent Number: 4,581,714

[45] Date of Patent: Apr. 8, 1986

[54] METHOD OF CALIBRATING AND LINEARIZING THE OUTPUT OF FLUID MEASURING INSTRUMENTS

[75] Inventor: Howard J. Reid, Brea, Calif.

[73] Assignee: Sensormedics Corporation, Anaheim, Calif.

[21] Appl. No.: 530,551

[22] Filed: Sep. 9, 1983

[51] Int. Cl.$^4$ .................. G06F 15/20; G06F 15/353; G01F 25/00

[52] U.S. Cl. .................................. 364/571; 364/573; 364/582

[58] Field of Search ................ 364/571, 573, 581, 582

[56] References Cited

U.S. PATENT DOCUMENTS

| | | | |
|---|---|---|---|
| 4,064,396 | 12/1977 | Panarello | 364/573 |
| 4,200,933 | 4/1980 | Nickel et al. | 364/573 X |
| 4,238,830 | 12/1980 | Unvala | 364/573 |
| 4,282,578 | 8/1981 | Payne et al. | 364/573 |
| 4,448,058 | 5/1984 | Jaffe et al. | 364/571 X |
| 4,460,967 | 7/1984 | Krull et al. | 364/571 X |
| 4,467,435 | 8/1984 | Warnke et al. | 364/571 X |
| 4,481,596 | 11/1984 | Townzen | 364/571 |

*Primary Examiner*—Felix D. Gruber
*Attorney, Agent, or Firm*—Lyon & Lyon

[57] ABSTRACT

A method for calibrating and linearizing the output of an instrument that includes a transducer having an output that is a nonlinear function of a property of interest of a fluid. The results of measurements performed on a plurality of transducers of the type to be used in the instrument are used to produce first and second equations which give the direct and inverse responses of a typical transducer. The results of further measurements on the particular transducer to be used in the instrument are used with the first equation to define how the second equation may be used to give accurate results with the particular transducer. The instrument is then calibrated and the results used with the second equation to produce an accurate linearized value for display as the output of the instrument.

22 Claims, 5 Drawing Figures

METHOD OF CALIBRATING AND LINEARIZING THE OUTPUT OF FLUID MEASURING INSTRUMENTS

BACKGROUND OF THE INVENTION

The present invention relates to fluid measuring instruments and is directed more particularly to a method of calibrating and linearizing the outputs of fluid measuring instruments which utilize transducers that have nonlinear responses.

In measuring the magnitude of a property of a fluid, such as the concentration or partial pressure of a component of interest, it is often necessary to utilize a transducer which has a nonlinear response. In non-dispersive infrared analyzers, for example, the concentration of a gas of interest is measured by means of a gas filled cell, commonly known as a Luft detector, which is illuminated by an infrared source through a sample cell that contains a gas of unknown composition. In such analyzers, the output of the Luft detector is an exponential (Beer's Law) function of the concentration of the gas of interest in the sample cell. Similar nonlinear responses are, however, exhibited by the transducers used in many other types of instruments, such as those which measure the temperature of a gas, the pH of a liquid, etc.

The nonlinearity of the response of many types of transducers creates a number of problems for the instruments in which they are used. One of these problems is that the nonlinearity prevents the property of interest from being determined by simply ratioing the output produced by the transducer during exposure to a sample fluid to the output produced by that transducer during exposure to a calibration fluid. This is because ratioing is a linear process and cannot therefore readily be used with nonlinear functions. Another of these problems is the loss of resolution that results from directly displaying the outputs of nonlinear transducers. Using a nonlinear display, for example, causes the resolution of the instrument to be greater at one end of the display range than at the other. Using a nonlinear display also introduces the inconvenience of having to interpolate between scale divisions of variable spacings.

The above-described problems are often dealt with by making use of linearization circuits. Analog linearization circuits, for example, make use of the nonlinear response of an analog circuit to compensate for the nonlinear response of the transducers with which they are used. Digital linearizing circuits make use of the mathematical processing ability of computerized instruments to solve equations which compensate for the nonlinear response of the detectors with which they are used. Linearizing circuits of the latter type can also operate by referencing look-up tables which are constructed from the equations to be solved.

While the above-mentioned types of linearizing circuits can operate with a moderate degree of accuracy, they can also introduce significant errors into the displayed outputs of the instruments with which they are used. These errors result from the fact that particular transducers often have nonlinear responses which differ from that of the typical transducer for which the linearizing circuit was designed. Such differences can, for example, result from differences in the sensitivity (or gain) of various transducers, or from differences in their zero responses or offsets. Such differences can also arise in a single transducer as its response changes with time, the accumulation of dirt deposits, etc. These differences produce errors by causing linearizing circuits to over- or under-correct for the response of the particular transducers with which they are used.

SUMMARY OF THE INVENTION

In accordance with the present invention there is provided an improved method for calibrating and linearizing the outputs of an instrument that uses nonlinear transducers which is not subject to the above-described problems and errors.

Generally speaking, the method of the present invention contemplates the production of two multi-term (preferably polynomial) equations which define the nonlinear response of a typical transducer of the type to be used in the instrument, the taking of measurements which determine the relationship between the response of the particular transducer to be used in the instrument and that of the typical transducer, and the utilization of the determined relationship and the equations to calibrate and linearize the output of the instrument. The use of this method assures the availability, at each calibration, of a linearizing function which accurately reflects the response of the particular transducer in its then current condition. The utilization of this linearizing function during both the calibration of the instrument and the making of measurements thereby, allows measurements upon the unknown fluid to be referenced to the result of calibration, without regard to the nonlinearity of the transducer response. An instrument which utilizes the calibration and linearization method of the invention is therefore able to provide accurate measurements with any of a variety of different transducers or with a transducer having a response which changes with time.

One particularly advantageous feature of the method of the invention is that it utilizes equations which describe the response of the transducer in two different ways. More particularly, the response of the transducer is described both in terms of a first equation which gives the output of the transducer as a function of the magnitude of the property of interest, and in terms of a second equation which gives the magnitude of the property of interest as a function of the output of the transducer. Because both of these equations represent the same response, they may be used interchangeably during the course of the calibration and linearization process. Each stage of the latter process may therefore use whichever equation most easily provides the information that is needed during that stage.

The availability of two different equations which describe the response of the transducer also makes it possible to determine the magnitude of the property of interest from the transducer output, or vice versa, without having to solve either equation for its roots. Since third and higher order equations may be evaluated much more easily than they may be solved, the practice of the invention provides its benefits without placing a high signal processing burden on the instrument. As a result, the nonlinear response of the transducer may be represented by equations having orders higher than those which could be used heretofore. This, in turn, makes possible the use of equations which more accurately represent the response of the transducer, thereby providing a more accurate linearization.

In the preferred embodiment, the method of the present invention also contemplates the determination and use of a scaling factor which assures that the maximum output of the nonlinear transducer does not cause the maximum signal processing capacity of the instrument to be exceeded. This scaling factor assures that the instrument is able to modify its use of the equations so as to provide the highest possible output resolution. The use of this scaling factor therefore makes it possible to service or replace a transducer without adversely affecting the resolution of the instrument in which it is used.

DESCRIPTION OF THE DRAWINGS

Other objects and advantages of the present invention will be apparent from the following description and drawingss in which.

DESCRIPTION OF THE PREFERRED EMBODIMENT

Figure 1:
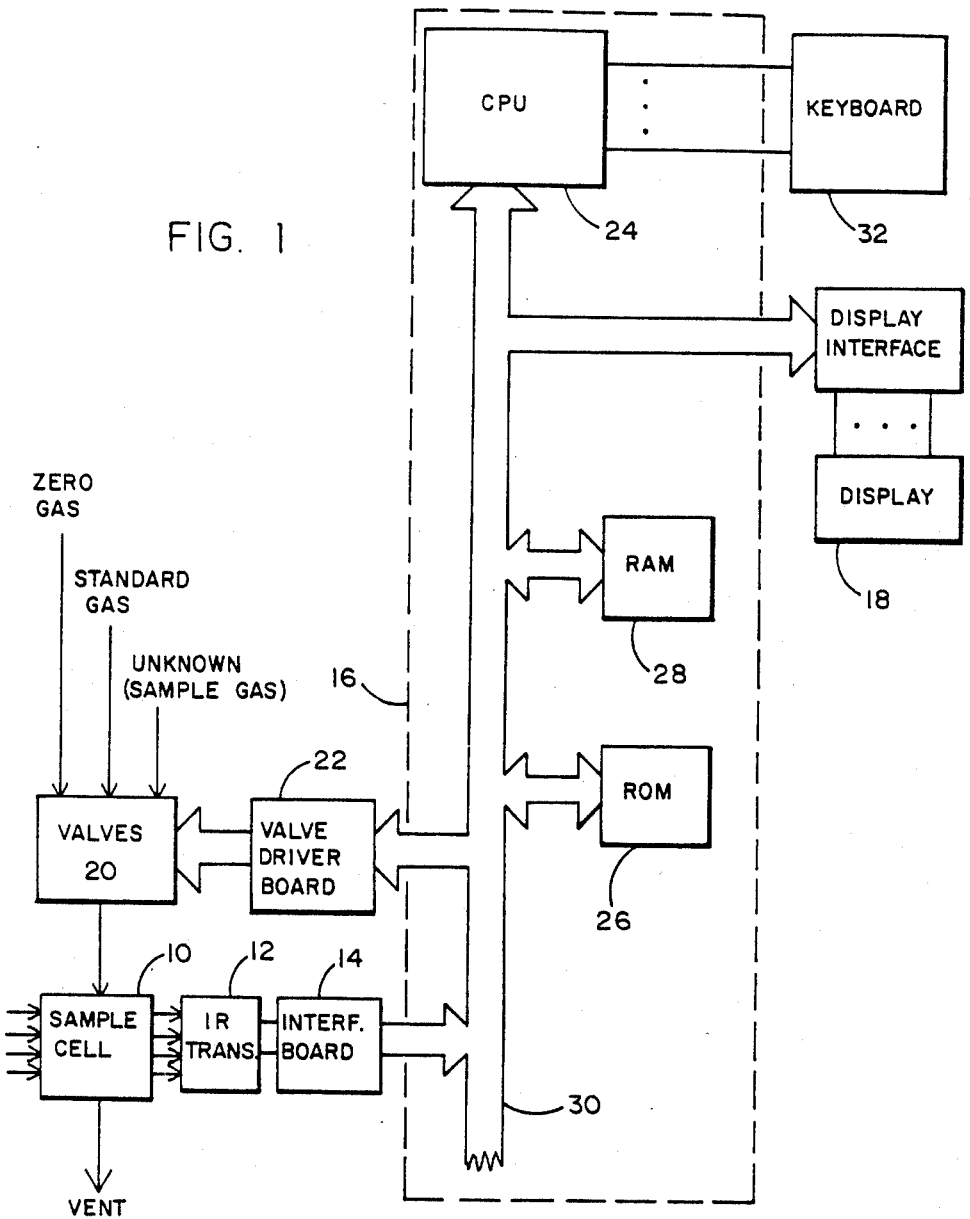
FIG. 1 is a block diagram of one type of instrument that is suitable for use in practicing the method of the present invention.

Referring to FIG. 1, there is shown a block diagram of a typical instrument of a type which is suitable for use in practicing the method of the invention. In FIG. 1 the instrument is of the type which measures the concentration (or partial pressure) of one gas in another by measuring the quantity of infrared radiation that is absorbed by the gas of interest as it flows through a sample cell that is illuminated by an infrared source of known intensity. Instruments of this type are commonly referred to as non-dispersive infrared analyzers. In general, however, the method of the invention may be applied to any instrument in which the magnitude of a property of interest of a fluid is measured by a transducer that has a nonlinear response to that property.

The analyzer of FIG. 1 includes a sample cell 10 for conducting a flow of the gas upon which measurements are to be made. As the gas flows through the sample cell, a beam of infrared radiation from a source (not shown) is transmitted therethrough through windows which are transparent to the portion of the infrared spectrum that is being used for the measurement. The quantity of radiation that is not absorbed by the gas of interest within the sample cell is measured by means of a suitable infrared transducer 12 which may comprise a Luft detector. The output of this detector is preferably demodulated and digitized in a signal interface board 14 before being communicated to a suitable digital computer 16 for further processing and/or for display on a human readable display 18.

In order to assure that the instrument accurately measures the concentration of the gas of interest, it is necessary to calibrate the instrument by measuring its response to the flow of a gas having none of the gas of interest (zero gas) and a gas having a known non-zero concentration of the gas of interest (standard or calibration gas). These gases are applied to the sample cell through a set of valves 20 which are controlled by computer 16 through a suitable valve driver board 22. Computer 16 also operates through valve driver board 22 and valve set 20 to control the flow of the unknown or sample gas through sample cell 10 after the calibration process has been completed. The sequence in which the valves of valve set 20 are operated, and the manner in which the output of transducer is received and processed are controlled by computer 16 in accordance with its stored program. A flow chart for the program by which computer 16 controls the operation of devices 10-22 in order to achieve the objectives of the invention will be described later in connection with FIGS. 3 and 4.

Computer 16 may comprise a conventional single board digital microcomputer of any of a variety of types. This computer includes a central processing unit or CPU 24 for performing sequencing and data processing operations, a read-only memory or ROM 26 for storing the program to be executed by CPU 24 and a read-write memory or RAM 28 for storing intermediate results and changeable program values and addresses. CPU 24 communicates with ROM 26, RAM 28 and the external devices with which it operates through a bidirectional multi-bit data/address bus 30. CPU 24 may also, however, communicate directly with certain peripheral devices, such as an operator keyboard 32, if it is provided with a port through which it can interface with such external devices. Because the internal structure and operation of a computer of the type shown in FIG. 1 is well known to those skilled in the art, it will not be described in detail herein.

Figure 2A:
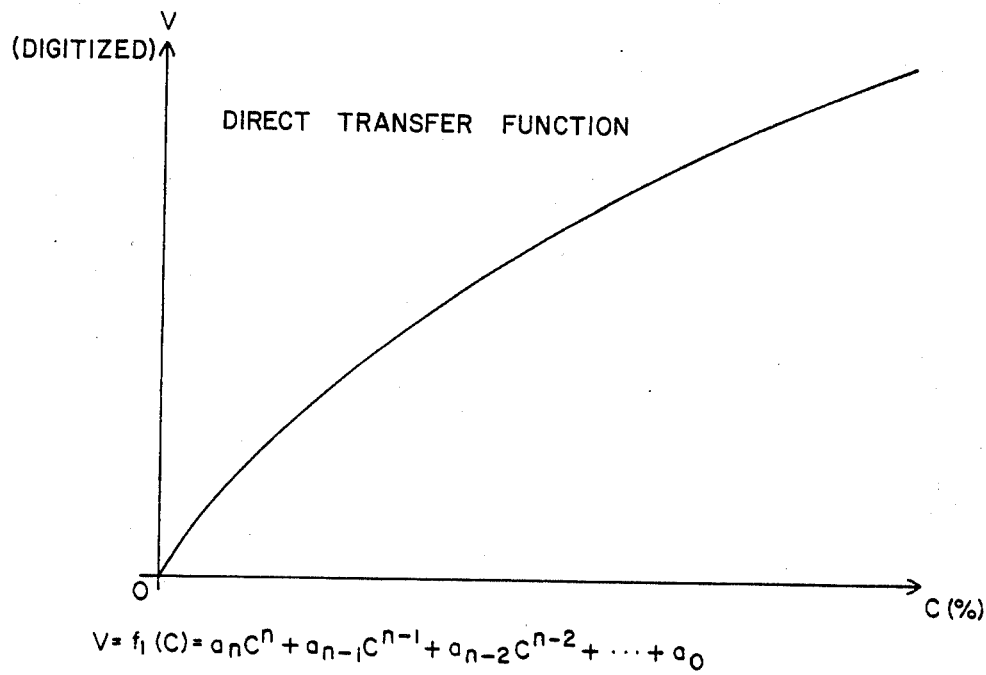
FIGS. 2a and 2b comprise two graphical and mathematical representations of the response of the transducer used in the instrument of FIG. 1.
Figure 2B:
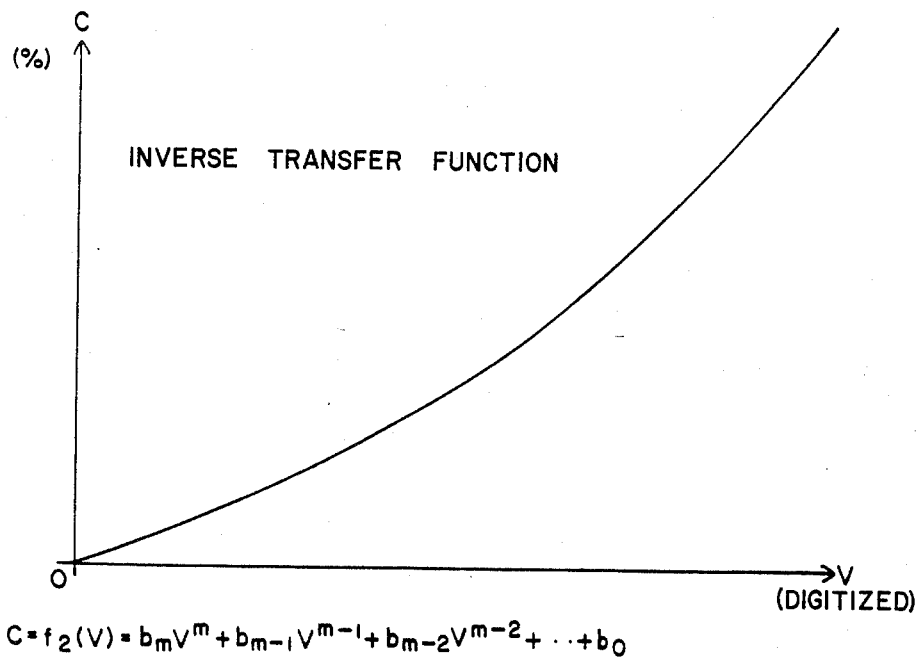

As is well known, there is a nonlinear relationship between the output of an infrared transducer, such as Luft detector 12 of FIG. 1, and the concentration of the gas of interest within the associated sample cell. The nonlinearity of this response is illustrated by the curves shown in FIGS. 2a and 2b. In FIG. 2a this response is plotted in terms of the demodulated, digitized output voltage V of transducer 12 (expressed in digital counts) as a function of the concentration C of the gas of interest within the sample cell (expressed as a %). In FIG. 2b this nonlinear response is plotted in terms of the concentration C of the gas of interest as a function of the demodulated, digitized output voltage V of transducer 12. For the sake of convenience, a response curve of the type shown in FIG. 2a will be referred to as defining the direct (or forward) response of the transducer, and a response curve of the type shown in FIG. 2b will be referred to as defining the inverse (or reverse) response of the transducer. As will be explained more fully presently, the method of the present invention makes use of both of the direct and inverse response characteristics of the transducer in calibrating the instrument and linearizing data produced thereby.

Because of normal manufacturing variations in the dimensions and compositions of different infrared transducers, the response of a particular transducer may be different from the response shown in FIGS. 2a and 2b. A particular transducer may, for example, have a sensitivity or gain which causes its output to be greater or less than that shown in FIG. 2a for a given concentration of the gas of interest, and/or a response which does not pass through the zero of the axis system. Because of the broad similarity of the responses of transducers of the same type, however, it is possible to define the response of a particular transducer in terms of (i) the response of a typical transducer, and (ii) the relationship between the response of a particular transducer and that of the typical transducer. In accordance with the present invention, there is provided a method which determines items (i) and (ii) and then uses the same to calibrate the instrument for operation with the particular transducer. After calibration, these items are used further to linearize the output of the particular transducer and thereby provide an instrument output of improved accuracy and repeatability.

In providing the above-mentioned advantages, the method of the invention contemplates the performance of the following steps. Firstly, there is produced a first equation which gives the direct response of a typical transducer of the type that is to be used in the instrument. In the course of performing this step, a series of measurements are performed on a plurality of representative (randomly selected) transducers of a type that are to be used in the instrument. This series of measurements is preferably made by applying to each of the plurality of transducers a sequence of gases having known concentrations of the gas of interest, and measuring the output voltages (counts) that are associated with those concentrations. After measurements have been performed on a sufficient number of transducers, the resulting data are plotted on the axes shown in FIG. 2a. Once this has been done, an equation that represents, or is characteristic of, the response or output of a typical transducer may be produced by fitting a selected type of curve to the plotted points. In the preferred embodiment, the selected type of curve is a polynomial equation of the type shown in FIG. 2a. The fitting of this curve is accomplished by selecting the value of n to be used in the equation, i.e., selecting the order of the equation, and then calculating the values of the coefficients such as "$A_n$" which minimize the difference between the curve representing the equation from the plotted points. Since such curve fitting procedures are well known to those skilled in the art, the application thereof will not be described in detail herein.

The next step in the practice of the method of the invention comprises the production of a second equation which gives the inverse response of a typical transducer of the type that is to be used in the instrument. This equation, the form of which is shown in FIG. 2b, may be produced in generally the same manner as the equation of FIG. 2a. More particularly, the equation may be produced by plotting the measured sets of points on the axes of FIG. 2b, and by fitting a selected type of curve to the plotted points using a conventional curve fitting technique. As is suggested by the use of different subscripts n and m in the equations of FIGS. 2a and 2b, both the coefficients and the exponents in the inverse response equation will ordinarily be different from those of the direct response equation. With one commonly used infrared transducer, for example, a third order (m=3) polynomial equation has been found adequate to represent the inverse response shown in FIG. 2b, but a fourth order (n=4) polynomial equation has been found necessary to adequately represent the direct response shown in FIG. 2a.

The production of equations which represent both the direct and inverse response characteristics of a typical transducer greatly facilitates the signal processing which is incident to the performance of the remaining steps of the method of the invention. This is because the availability of both equations makes it possible to determine either (a) the transducer output which corresponds to a given concentration of the component of interest, or (b) the concentration of the component of interest which corresponds to a given transducer output, without having to solve either of the two equations for its roots. Stated differently, the transducer output which corresponds to a given concentration of the gas of interest, or the concentration which corresponds to a given transducer output may be determined by merely substituting the available one of these variables into the appropriate one of the two equations, and then evaluating that equation by multiplying out and adding together its various terms. Moreover, since both equations represent the response of the same transducer, they may be utilized interchangeably at vraious stages of the calibration and linearization processes, depending upon which equation then most conveniently provides the information that is needed from the information that is then available. The reasons why it is desirable to use different equations at different stages of the calibration and linearization process will be apparent from the following description of the manner in which the method of the invention makes use of the equations of FIGS. 2a and 2b.

Once the equations which give the direct and inverse response characteristics of a typical detector have been produced, they are made available to the instrument by storing them within computer 16. If the instrument is used with only a single type of transducer, this may be accomplished by storing the two equations for that type of transducer in ROM 26. If, however, the instrument is to be utilized with different types of transducers, the equations for those types of transducers may be entered via keyboard 32 and stored in RAM 28. Once these equations are stored in the computer, the remainder of the method of the invention may be practiced by causing the computer to execute the program depicted in FIG. 3.

Upon beginning the execution of the program shown in FIG. 3, the computer first encounters a block 40 which causes it to read the known concentration value $C_{s1}$ of the standard gas which will later be applied to the sample cell through valve set 20. If the instrument is always used with a standard gas of the same concentration, this concentration may be permanently stored in ROM 26. Alternatively, if the instrument is to be used with standard gases having a variety of different concentration values (e.g., values which depend upon the type of transducer being used), the concentration of the standard gas may be entered by the operator via keyboard 32.

After completing the operation called for by block 40, the computer proceeds to a block 42 which causes it to apply a suitable zero gas to sample cell 10 and read the resulting output $V_O$ of transducer 12. The result of the performance of this step is the determination of the value of any offset or zero offest between the output of transducer 12 and the output of a typical transducer of its type. By determining this zero offset, the computer makes available to itself one of the two quantities that are needed in order to correct for differences between the actual response of transducer 12 and the estimated response thereof that is predicted by the two stored equations. The ability of the computer to correct for a zero offset also makes it possible to correct for any DC bias which is introduced by the circuitry of interface board 14. Such a DC bias may, for example, be desirable to assure that the A/D converter need not handle both positive and negative signal voltages.

After determining the offset of the transducer, the computer proceeds to a block 44. Upon encountering this block, the computer is directed to apply the standard gas to the sample cell, and to read the actual transducer output signal $V_{SA}$ which is associated with the standard gas. Thereafter, upon encountering block 46, the computer is directed to substitute the known concentration $C_{S1}$ of the standard gas into the direct transfer function equation (FIG. 2a) and evaluate the same in order to determine the calculated or estimated transducer output signal $V_{SE}$ which is associated with the standard gas.

Once both the actual and estimated transducer output signals are available, the computer proceeds via block 48 to determine the relative sensitivity of the particular transducer, i.e., its sensitivity with respect to that of the typical transducer. This is done by calculating the ratio K of the estimated transducer output signal to the actual transducer output signal, after the latter has been corrected for offset voltage $V_O$. By determining the latter ratio, the computer makes available to itself the second of the two quantities that are needed in order to correct for differences between the actual response of the particular transducer and the estimated response thereof that is predicted by the two stored equations. The manner in which sensitivity ratio K and offset voltage $V_O$ are used in this connection will be described later.

Upon encountering blocks 50 and 52, the computer performs a series of operations which result in a determination of the scaling factor $K'$ which is necessary in order to assure that the signal processing capacity of the instrument of FIG. 1 is not exceeded when the transducer produces its maximum output signal $V_{MAX}$. The determination of this scaling factor is desirable because it defines the amplification (or attenuation) that may be safely provided during signal processing. Such amplification (or attenuation) is desirable because it assures that the instrument is operating at its highest potential resolution, thereby assuring a more accurate output reading.

The determination of scaling factor $K'$ begins as the computer encounters block 50 and is directed to evaluate the inverse transfer function equation (FIG. 2b) at maximum transducer output $V_{MAX}$ (as corrected for sensitivity ratio K) to determine the maximum concentration $C_{MAX}$ that is to be processed by the instrument. Note that this operation is performed by simply evaluating the inverse transfer function equation at the then available value of independent variable V, and is analogous to the operation performed via block 46 using the direct transfer function equation and the then available value of independent variable C.

The determination of scaling factor $K'$ then continues as the computer encounters block 52 and is directed to determine the ratio of the signal processing capacity $V_{cap}$ of the instrument and maximum concentration $C_{MAX}$. (One factor that limits the processing capacity of the instrument is the number of bits in the digital words used therein.) In forming this ratio, the factor 0.95 is inserted to provide a margin of safety which assures that the capacity of the instrument is not exceeded as a result of rounding errors.

Once scaling factor $K'$ has been determined, the computer is directed to a block 54 which causes it to modify or reformulate the inverse transfer function equation so as to correct for the values of offset $V_O$, sensitivity ratio K, and scaling factor $K'$. The effect of this reformulation generates a linearizing function which allows the response of the particular transducer to be expressed in terms of the equation for a typical transducer.

Once this linearizing equation is available, the instrument is calibrated by causing the computer to carry out the steps called for by blocks 56 and 58. Block 56 causes the computer to apply to the sample cell a suitable calibration gas, which may (but need not) be the same as the standard gas used in connection with block 44, and to measure the resulting output $V_C$ of transducer 12. Then, via block 58, the linearizing equation is evaluated for transducer output $V_C$ to determine the calculated calibration gas concentration value $C_C$ which is associated therewith. As will be explained more fully presently, calculated concentration value $C_C$ serves as a standard to which the calculated concentrations of gases of unknown composition may be referenced to determine the concentrations to be displayed at the output of the instrument. Because this calculation process takes into account the nonlinearity of the transducer response, the result of the calculation is free of any nonlinearity and may therefore be used as the linearized concentration value of the component of interest in the calibration gas.

Figure 3:
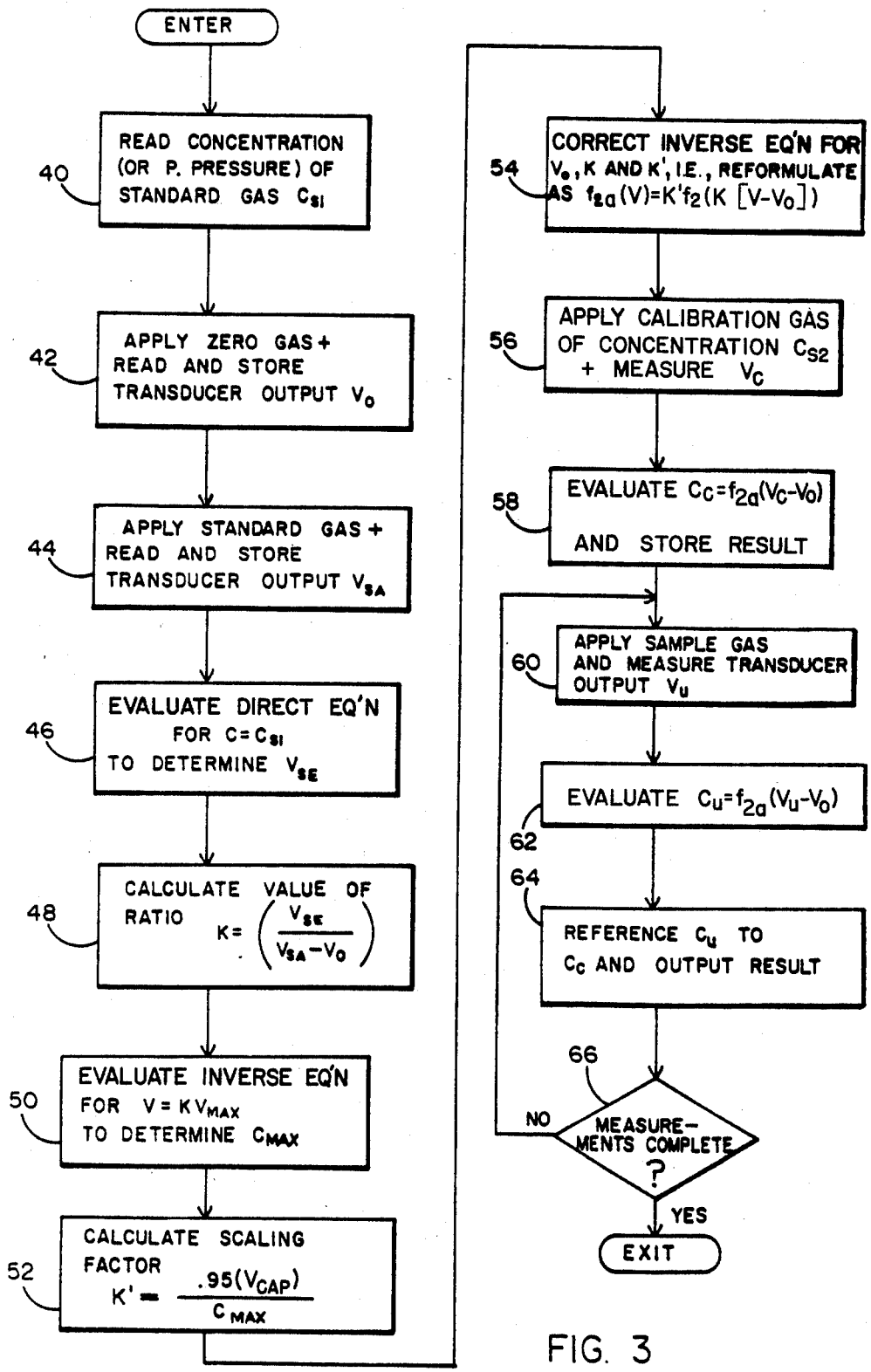
FIG. 3 is a flow chart which depicts the computer executable parts of the method of the present invention.

Following the completion of the calibration process, the instrument is ready to proceed with the making and linearization of a series of measurements on gases of unknown composition by repeatedly executing a measurement loop which includes blocks 60–66 of FIG. 3. In doing so, the computer first encounters a block 60 which causes it to apply the sample gas to the sample cell and measure the resulting transducer output $V_u$. Thereafter, upon encountering block 62 the computer evaluates the linearizing equation for $V = V_u$ to determine the calculated concentration value $C_u$ that is associated therewith. Because the calculation of concentration $C_u$ takes into account the nonlinearities of the transducer, it is free of any nonlinearity and may therefore be used as the linearized concentration value of the component of interest in the sample gas.

After linearized concentration values $C_C$ and $C_u$ are both available, the computer proceeds to a block 64 which causes it to reference unknown concentration value $C_u$ to known concentration value $C_C$ and thereby produce a concentration value $C_{out}$ for outputting on display 18. This referencing is preferably accomplished by taking the ratio of $C_u$ to $C_C$ and then multiplying the result by the known concentration of the calibration gas $C_{S2}$. This use of a simple ratioing step to produce the final output is valid because both of the values used in the ratio have been linearized and may therefore be directly compared to one another in the linear domain.

Upon completing and displaying of the results of the first measurement, the computer proceeds to a decision block 66 which causes it to determine whether or not all of the desired measurements requested by the user have been completed. If all measurements have not been completed, the computer is directed back to block 60 to repeat the measurement process on the then available sample gas. If, for example, the sample gas is the gas produced by the operation of a continuous process, the measurement loop may be executed one or more times each second to provide a substantially continuous current indication of the concentration of the component of interest in the process gas. In such cases decision block 66 may serve to cause the computer to repeat the measurement process until it encounters a stop command entered by the operator through keyboard 32. Upon the completion of the desired series of measurements, or upon the receipt of a stop command, the computer will exit the measurement loop and thereby terminate the measurement process.

In spite of the fact that the practice of the method of the invention involves evaluating rather than solving of the nonlinear equations which describe the response of the transducer, appreciable amounts of time may be involved in performing the multiplications and additions that are involved in executing the measurement loop. In cases in which the time involved in this execution is objectionable, the execution may be speeded up by using the steps shown in the flow chart of FIG. 4. The latter flow chart depicts an alternative method for evaluating the linearizing equation of block 54, those blocks which perform the same steps in FIGS. 3 and 4 being similarly numbered.

Figure 4:
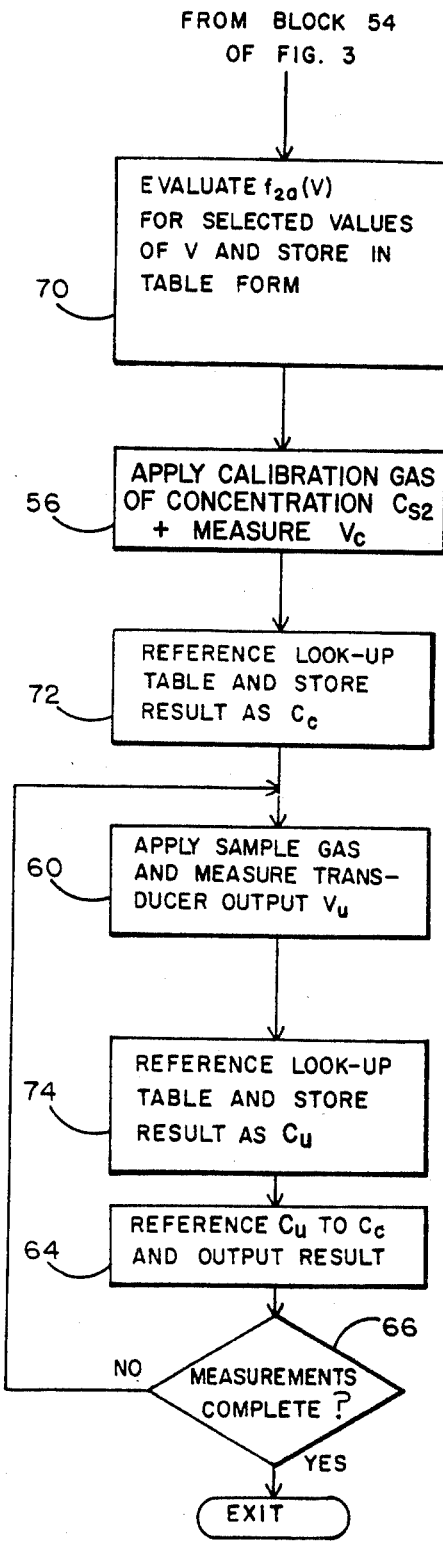
FIG. 4 is a partial flow chart which depicts an alternative computer executable part of the method of the invention.

The principal difference between the flow chart of FIG. 4 and that of FIG. 3 is that, in the flow chart of FIG. 4, the linearizing second equation is evaluated by reference to a look-up table rather than by repeated multiplications and additions. In the flow chart of FIG. 4, this look-up table is constructed as the computer encounters a block 70 which causes it to (i) evaluate the reformulated second equation for a number of assumed values V which is equal to the number of entries to be included in the table, and (ii) store the resulting evaluations in tabular form.

Once the look-up table has been constructed and stored, the computer proceeds to block 56, which causes it to calibrate the instrument in the manner described in connection with FIG. 3. After doing so, however, the instrument determines linearized concentration value $C_C$ by referencing the look-up table rather than by evaluating an equation. The computer then enters the measurement loop, including the blocks 60-74-64, to proceed with the taking of measurements on the sample gas. In executing this measurement loop, the linearized concentration value $C_u$ that is associated with the sample gas is again determined with reference to the look-up table rather than by the evaluation of an equation. Naturally, because a look-up table may be referenced more quickly than an equation may be evaluated, the measurement loop of the flow chart of FIG. 4 may be executed in a much shorter time than that of the embodiment of FIG. 3. The method depicted in the flow chart of FIG. 4 may therefore be used in applications in which measurements must be made much more rapidly than those which can be made using the method depicted in the flow chart of FIG. 3.

A possible disadvantage of the embodiment of FIG. 4 is that, because look-up tables include only a discrete number of entries, many of the desired values will fall between the available table entries. It may therefore be necessary to include in the measurement loop steps that allow the interpolation of values between the available table entries. While the time necessary to perform these interpolation steps occupies part of the time saved in eliminating the evaluation of the polynomial equation, it does not occupy so much of that time that the use of the embodiment of FIG. 4 becomes unattractive in comparison with the use of the embodiment of FIG. 3. In other words, even with the inclusion of interpolation steps, the measurement loop of the embodiment of FIG. 4 may be executed more rapidly than that of the embodiment of FIG. 3.

In view of the foregoing, it will be seen that the calibration and linearization method of the present invention provides a number of advantages over previously known calibration and/or linearization methods. Firstly, the method of the invention assures that calibration and linearization reflect both the actual response of the particular transducer that is selected for use in the instrument, and the response of a typical transducer of the selected type. Secondly, the method of the invention provides the benefits of linearization without requiring the solution of an equation that represents response of the transducer that is used in the instrument. Finally, the method of the invention contemplates the referencing of measured values to calibration values only after both values have been linearized in accordance with the abovementioned equations. Together these features of the method of the invention assure that the outputs of instruments that are calibrated and linearized in accordance therewith are more accurate and more linear than those of instruments that are calibrated and linearized in accordance with previously known methods.

What is claimed is:

1. A method of calibrating and linearizing the output of an instrument that includes a particular transducer having an output that is a non-linear function of a concentration of a component of interest in a fluid, comprising:
   (a) producing a first equation which is characteristic of the output of a typical transducer of the type to be used in the instrument as a function of the concentration of the component of interest,
   (b) producing a second equation which gives the concentration of the component of interest as a function of the output of said typical transducer,
   (c) applying a first fluid having a known non-zero concentration of the component of interest to the particular transducer to be used in the instrument and measuring the actual output thereof,
   (d) substituting a value corresponding to said known concentration into the first equation and evaluating the first equation to determine the estimated output of said typical transducer,
   (e) using said actual and estimated outputs to determine the relative sensitivity of the particular transducer,
   (f) applying a second fluid having a known nonzero concentration of the component of interest to the particular transducer and measuring the actual output thereof,
   (g) correcting the measured output of step (f) for said relative sensitivity and using the result and the second equation to produce the linearized concentration value corresponding to the concentration of said second fluid,
   (h) applying a sample fluid having an unknown concentration of the component of interest to the particular transducer and measuring the actual output thereof,
   (i) correcting the measured output of step (h) for said relative sensitivity and using the result and the second equation to produce the linearized concentration value corresponding to the concentration of said sample fluid, and
   (j) referencing the concentration value of step (i) to that of step (g) and displaying the result as the concentration of the component of interest in the sample fluid.

2. The method of claim 1 in which step (j) is performed by multiplying the ratio of said linearized concentration values by the concentration of the component of interest in the second fluid.

3. The method of claim 1 in which the first and second linearized concentration values are produced by substituting the corrected measured outputs produced in steps (g) and (i) into the second equation and then evaluating that equation.

4. The method of claim 1 in which the first and second linearized concentration values are produced by utilizing the second equation to construct a look-up table and then addressing said look-up table with the corrected measured outputs produced in steps (g) and (i).

5. The method of claim 1 in which said first and second fluids have the same concentration of the component of interest.

6. The method of claim 1 in which step (e) comprises taking the ratio K of said estimated output to said measured output.

7. The method of claim 6 in which the correcting steps of steps (g) and (i) comprise the multiplication of the measured output by ratio K.

8. The method of claim 1 in which at least one of the first and second equations is produced by:
  (i) performing a plurality of measurements on each of a plurality of transducers of the type to be used in the instrument,
  (ii) selecting an equation of the type that is to be used in representing the response of a typical one of said transducer, said equation including at least one term with an unknown coefficient, and
  (iii) determining the values of said coefficients which most closely fit said equation to the results of said plurality of measurements.

9. A method of calibrating and linearizing the output of an instrument that includes a particular transducer having an output that is a non-linear function of the concentration of a gas of interest, comprising:
  (a) producing a first polynomial equation which is characteristic of the output of a typical transducer of the type to be used in the measurement as a function of the concentration of the gas of interest,
  (b) producing a second polynomial equation which gives the concentration of the gas of interest as a function of the output of said typical transducer,
  (c) applying a gas having substantially none of the gas of interest to the particular transducer to be used in the instrument, measuring the resulting output thereof, and storing that output for use as a zero correction value,
  (d) applying a first gas having a first known nonzero concentration of the gas of interest to the particular transducer and measuring the actual output thereof,
  (e) substituting a value corresponding to said first concentration into said first equation and evaluating the first equation to determine the estimated output of the typical transducer,
  (f) subtracting the zero correction value from the actual output of the particular transducer to produce a zerocorrected actual output,
  (g) using said estimated output and the zerocorrected actual output to determine the relative sensitivity of the actual transducer,
  (h) applying a second gas having a second known non-zero concentration of the gas of interest to the particular transducer and measuring the actual output thereof,
  (i) correcting the measured output of step (h) for the zero correction value and said relative sensitivity, and using the result and the second equation to produce the linearized concentration value corresponding to said second concentration,
  (j) applying a sample gas having an unknown concentration of the gas of interest to the particular transducer and measuring the actual output thereof,
  (k) correcting the measured output of step (j) for the zero correction value and said relative sensitivity, and using the result and the second equation to produce the linearized concentration value corresponding to said unknown concentration, and
  (l) producing an output signal that is indicative of the ratio of said linearized concentration values and said second concentration.

10. The method of claim 9 in which the first and second linearized concentration values of steps (i) and (k) are produced by substituting the zero-corrected measured output values into the second equation and then evaluating the same.

11. The method of claim 9 in which the linearized concentration values of steps (i) and (k) are produced with reference to a look-up table constructed by evaluating the second equation for a plurality of assumed output values.

12. The method of claim 9 in which the first and second gases are the same gas.

13. The method of claim 9 in which the second equation is multiplied by a scaling factor prior to its use in steps (i) and (k), said scaling factor being a number which assures that the signal processing capacity of the instrument is not exceeded when the transducer produces its maximum output.

14. A method of calibrating and linearizing the output of an instrument that includes a particular transducer having an output V that is a non-linear function of the magnitude C of a property of interest of a fluid, comprising:
  (a) performing a series of measurements on each of a plurality of transducers of the type to be used in the instrument,
  (b) selecting a first equation $V = f_1(C)$ of a type that is suitable for use in representing the response of a typical one of said transducers, where $f_1$ is a first function having at least one unknown coefficient,
  (c) selecting a second equation $C = f_2(V)$ of a type that is suitable for use in representing the inverse response of the typical one of said transducers, where $f_2$ is a second function having at least one unknown coefficient,
  (d) determining the values of the unknown coefficients of the first function to adapt said first equation to represent the response of the typical transducer,
  (e) determining the values of the unknown coefficients of the second function to adapt said second equation to represent the inverse response of the typical transducer,
  (f) applying to the particular transducer a fluid having substantially a zero magnitude of the property of interest and measuring the output $V_o$ thereof,
  (g) applying to the particular transducer a first fluid having a first known magnitude $C_{s1}$ of the property of interest and measuring the actual output $V_{sa}$ thereof,
  (h) substituting $C_{s1}$ into the first equation and evaluating the first equation to determine the estimated output $V_{se}$ of said particular transducer,
  (i) determining the ratio K of $V_{se}$ to $V_{sa} - V_o$,
  (j) applying to the particular transducer a second fluid having a second known magnitude $C_{s2}$ of the property of interest and measuring the actual output $V_c$ thereof, (k) using the second equation to determine the value of $C_c$, which corresponds to $V = K(V_c - V_o)$, (l) applying to the particular transducer a fluid having an unknown magnitude of the property of interest and measuring the actual output $V_u$ thereof, (m) using the second equation to determine the value $C_u$ which corresponds to $V = K(V_u - V_o)$ and (n) producing as an output a signal indicative of the value $C_{out}$, where $C_{out} = C_u(C_{s2}/C_c)$.

15. The method of claim 14 in which the first fluid is the same as the second fluid.

16. The method of claim 14 in which values $C_c$ and $C_u$ are determined with reference to a look-up table constructed by evaluating the second equation for a plurality of assumed values of V.

17. The method of claim 14 in which values $C_c$ and $C_u$ are determined by evaluating the second equation for the values $V = K(V_c - V_o)$ and $V = K(V_u - V_o)$, respectively.

18. The method of claim 14 in which the second equation is multiplied by a scaling factor $K'$ prior to its use in steps (j) and (l), $K'$ being a number which assures that the signal processing capacity of the instrument is not exceeded when the transducer produces its maximum output.

19. A method of calibrating and linearizing the output of an instrument that includes a particular transducer having an output V that is a non-linear function of the magnitude C of a property of interest of a fluid, comprising:

(a) performing a series of measurements on each of a plurality of transducers of the type to be used in the instrument, (b) selecting a first equation $V = f_1(C)$ of a type that is suitable for use in representing the response of a typical one of said transducers, where $f_1$ is a first function having at least one term with an unknown coefficient, (c) selecting a second equation $C = f_2(V)$ of a type that is suitable for use in representing the inverse response of the typical one of said transducers, where $f_2$ is a second function having at least one term with an unknown coefficient, (d) determining the values of the unknown coefficients of the first function to adapt said first equation to represent the response of the typical transducer, (e) determining the values of the unknown coefficients of the second function to adapt said second equation to represent the inverse response of the typical transducer, (f) applying a fluid for which C is substantially equal to zero to the particular transducer and measuring and storing the resulting output $V_o$ thereof, (g) applying to the particular transducer a first fluid having a first known magnitude $C_{s1}$ of the property of interest and measuring the actual output $V_{sa}$ thereof, (h) substituting $C_{s1}$ into the first equation and evaluating the first equation to determine the estimated output $V_{se}$ of said typical transducer, (i) determining the ratio $K = V_{se}/(V_{sa} - V_o)$, (j) evaluating the second equation for $C_{max} = f_2(KV_{max})$ where $V_{max}$ is the maximum output of the typical transducer, (k) determining the ratio $$K' = 0.95(V_{cap})/C_{max}$$

where $V_{cap}$ is the maximum V value which can be handled by the instrument, (l) reformulating the second equation as $$C = K' f_2(K[V - V_o]),$$

(m) applying to said particular transducer a second fluid having a second known magnitude $C_{s2}$ of the property of interest and measuring the output $V_c$ thereof, (n) using the reformulated second equation to determine the linearized value $C_c$ which corresponds to $V = V_c$, (o) applying to the particular transducer a sample fluid having an unknown magnitude of the property of interest and measuring the output $V_u$ thereof, (p) using the reformulated second equation to determine the value $C_u$ which corresponds to $V = V_u$, and (q) producing as an output a signal indicative of the value $C_{out}$ where $C_{out} = C_u(C_{s2}/C_c)$.

20. The method of claim 19 in which said first and second fluids have the same magnitude of the property of interest.

21. The method of claim 19 in which steps (n) and (p) are performed by substituting the measured outputs into the reformulated second equation and then evaluating the same.

22. The method of claim 19 in which steps (n) and (p) are performed by referencing a look-up table constructed by evaluating the reformulated second equation for a plurality of assumed values of V.

* * * * *